United States Patent
Schuetz et al.

(10) Patent No.: US 8,415,422 B2
(45) Date of Patent: Apr. 9, 2013

(54) (METH)ACRYLATE MONOMER, POLYMER AND COATING AGENT

(75) Inventors: Thorben Schuetz, Seeheim-Jugenheim (DE); Joachim Knebel, Alsbach-Haehnlein (DE); Mario Gomez Andreu, Pfungstadt (DE); Ralf Jackstell, Rostock (DE); Matthias Beller, Nienhagen (DE); Anne Grotevendt, Malchin (DE); Christine Maria Breiner, Laudenbach (DE)

(73) Assignee: Evonik Röhm GmbH, Darmstadt (DE)

( * ) Notice: Subject to any disclaimer, the term of this patent is extended or adjusted under 35 U.S.C. 154(b) by 0 days.

(21) Appl. No.: 13/058,103

(22) PCT Filed: Aug. 31, 2009

(86) PCT No.: PCT/EP2009/061178
§ 371 (c)(1), (2), (4) Date: Feb. 8, 2011

(87) PCT Pub. No.: WO2010/026119
PCT Pub. Date: Mar. 11, 2010

(65) Prior Publication Data
US 2011/0130509 A1   Jun. 2, 2011

(30) Foreign Application Priority Data
Sep. 8, 2008  (DE) .................. 10 2008 046 075

(51) Int. Cl.
| C08L 33/14 | (2006.01) |
| C08L 67/07 | (2006.01) |
| C08F 20/28 | (2006.01) |
| C08F 8/30  | (2006.01) |
| C08F 8/32  | (2006.01) |
| C07C 69/54 | (2006.01) |

(52) U.S. Cl. ........ 524/539; 524/558; 526/315; 525/376; 525/382; 560/205

(58) Field of Classification Search .................. 524/539, 524/558; 525/376, 382; 526/315; 560/205
See application file for complete search history.

(56) References Cited

U.S. PATENT DOCUMENTS
6,177,510 B1   1/2001  Saam

FOREIGN PATENT DOCUMENTS
EP   1 044 993        10/2000
EP   1044993 A1   *  10/2000

OTHER PUBLICATIONS

Database Beilstein [Online], Beilstein Institute for Organic Chemistry, Frankfurt-Main, DE; XP002551332; Citation No. 1189150; & Berlin et al: Sb. Statei Obshch. Khim., 1953, pp. 1560-1561, XP00811368.*
U.S. Appl. No. 13/257,178, filed Sep. 16, 2011, Maus, et al.
Berlin et al., "Sb. Statei Obshch. Khim", Beilstein Institute for Organic Chemistry, pp. 1560-1561 (1953) XP-002551332.
International Search Report Issued Nov. 16, 2009 in PCT/EP09/061178 filed Aug. 31, 2009.
U.S. Appl. No. 13/055,624, filed Jan. 24, 2011, Breiner, et al.
U.S. Appl. No. 13/058,149, filed Feb. 8, 2011, Schuetz, et al.

* cited by examiner

*Primary Examiner* — Michael M Bernshteyn
(74) *Attorney, Agent, or Firm* — Oblon, Spivak, McClelland, Maier & Neustadt, L.L.P.

(57) ABSTRACT

The present invention relates to a (meth)acrylate monomer of the general formula (I)

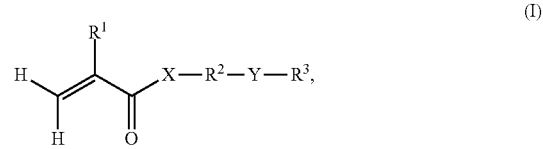

in which $R^1$ is hydrogen or a methyl group, X is oxygen or a group of the formula NR' in which R' is hydrogen or a radical having 1 to 6 carbon atoms, $R^2$ is an alkylene group having 1 to 22 carbon atoms, Y is oxygen, sulphur or a group of the formula NR", in which R" represents hydrogen or a radical having 1 to 6 carbon atoms, and $R^3$ is an unsaturated radical having 8 carbon atoms and at least two double bonds.

The present invention further relates to a process for preparing the monomers set out above, to polymers obtainable from this monomer mixture, and to coating materials which comprise the stated polymers.

22 Claims, No Drawings

(METH)ACRYLATE MONOMER, POLYMER AND COATING AGENT

The present invention relates to a (meth)acrylate monomer and also to a monomer mixture which comprises a (meth)acrylate monomer. The present invention is further directed to a polymer obtainable using said monomer and/or said monomer mixture. The present invention further relates to a coating material.

Coating materials, more particularly paints and varnishes, have for a long time been produced synthetically. Many of these coating materials are based on what are called alkyd resins, which are prepared using polyfunctional acids, alcohols and fatty acids and/or fatty acid derivatives. One particular group of these alkyd resins forms crosslinked films on exposure to oxygen, the crosslinking taking place by oxidation with participation of unsaturated groups. Many of these alkyd resins include organic solvents or dispersants to allow the resins to be applied in a thin film to objects to be coated. For reasons of environmental protection and of occupational safety, however, it is intended that the use of these solvents should be abandoned. Consequently, corresponding resins have been developed that are based on aqueous dispersions, but their stability on storage is limited. Moreover, the water uptake of many alkyd resins is too high, or their solvent resistance and their hardness are too low. Accordingly, attempts have been undertaken to replace or to modify the aforementioned conventional alkyd-based paints and varnishes.

Known by way of example from U.S. Pat. No. 4,010,126 are compositions which comprise an alkyd resin which is modified with (meth)acrylate polymers and which is subsequently used in an emulsion polymerization. The compositions described are prepared over several steps, and so the resins described are very costly and inconvenient to prepare.

A coating composition based on solution polymers, based on vinyl monomers, is described in DE-A-101 06 561, for example. This composition, though, has a high organic solvent content.

Furthermore, aqueous dispersions based on (meth)acrylate polymers are also known. For example, the publication DE-A-41 05 134 describes aqueous dispersions which can be used as binders in paints and varnishes. The preparation of these binders, however, takes place over several stages, involving first production of a solution polymer which, following neutralization, is used in an emulsion polymerization.

DE A 25 13 516, moreover, describes aqueous dispersions which comprise (meth)acrylate-based polymers, some of the (meth)acrylates being derived from unsaturated alcohol residues. A particular disadvantage of the dispersions described is their costly and inconvenient preparation, producing the (meth)acrylate-based polymers by solution polymerization. These polymers have a high acid group content, in the range from 5% to 20% by weight, based on the solution polymer.

The publication DE-A 26 38 544 describes oxidatively drying, aqueous dispersions which comprise emulsion polymers based on (meth)acrylates, with some of the (meth)acrylates used being derived from unsaturated alcohol residues. However, chain-transfer agents have been used in preparing the emulsion polymers, and so the solubility of the emulsion polymer is high.

Furthermore, aqueous dispersions which comprise oxidatively drying polymers are set out in F.-B. Chen, G. Bufkin, "Crosslinkable Emulsion Polymers by Autooxidation II", Journal of Applied Polymer Science, Vol. 30, 4551-4570 (1985). The polymers contain 2% to 8% by weight of units derived from (meth)acrylates with unsaturated, long-chain alcohol radicals. The durability of these dispersions and the hardness of the paint and varnish films are, for many applications, not sufficient.

The publication U.S. Pat. No. 5,750,751, moreover, describes polymers based on vinyl monomers which are able to crosslink at room temperature. The polymers may be obtained either by solution polymerization or by emulsion polymerization. The monomer mixtures to be polymerized may include, among others, (meth)acrylates whose alcohol residues have been modified with unsaturated fatty acids. The polymers obtained by solution polymerization and emulsion polymerization of modified (meth)acrylates exhibit a high solubility, owing to the use of chain-transfer agents. A disadvantage of the coating materials described by U.S. Pat. No. 5,750,751, however, is that it is necessary to add plasticizing solvents, which ought to be avoided on environmental grounds.

An improvement in this respect is obtained through the teaching of publication EP-A-1 044 993. This document describes aqueous dispersions based on (meth)acrylates. The mixtures for polymerization comprise (meth)acrylates modified with unsaturated fatty acids. A key aspect of this solution lies in the use of polymers which have a particularly broad molecular weight distribution, the number-average molecular weight being situated in the range from 300 to 3000 g/mol. A disadvantage of this system, however, is that the resulting films are, for many applications, too soft.

Additionally, document WO 2006/013061 describes dispersions which comprise particles based on (meth)acrylates. The monomer mixtures used for producing the particles comprise (meth)acrylates modified with unsaturated fatty acids. In the examples, however, there are no monomers polymerized that contain acid groups. Moreover, the fraction of (meth)acrylates modified with unsaturated fatty acids is very high. Particular disadvantages of the dispersions described in WO 2006/013061 are their complex preparation and the high fraction of residual monomers. Furthermore, the coatings obtained from the dispersions display poor stability towards certain solvents.

The prior art also, furthermore, discloses dispersions which as well as polymers based on (meth)acrylates may also comprise alkyd resins. By way of example the document WO 98/22545 describes polymers with units derived from (meth)acrylates with unsaturated alcohol residues. These polymers can be used together with alkyd resins.

However, solvents are used in order to produce paints and varnishes from the polymers described. Aqueous dispersions are not described in WO 98/22545. Consequently these compositions are hampered by the disadvantages set out above.

Moreover, Japanese publication 59011376 describes (meth)acrylate-based emulsion polymers. The dispersions, at a solids content of approximately 40%, have a dynamic viscosity of at least 200 mPas. The publication does not report a particle size. On the basis of the high viscosity of the dispersion, however, it can be assumed that the emulsion polymers have a particle size below 40 nm. A disadvantage of the dispersions described in this publication is their poor storability. It is found, furthermore, that the coatings obtained do not have sufficient stability for heightened requirements in respect of every solvent.

Furthermore, U.S. Pat. No. 6,599,972 discloses coating compositions based on polymers which in turn are based on (meth)acrylates whose alcohol residue derives from unsaturated fatty acid derivatives. Disadvantages of the coating compositions explicitly set out therein are their storability and also the stability of the coatings obtained from the compositions described.

(Meth)acrylate monomers which can be obtained by reacting 1,3-butadiene and (meth)acrylic acid are set out in publications including DE-A-19 43 453, U.S. Pat. No. 3,562,314 and Baibulatova et al., Zhurnal Organicheskoi Khimii (1982), 18(1), 46-52. However, there is no description of coating materials obtainable with these monomers. Instead, only applications in lubricants are set out. Also set out is the fact that the (meth)acrylate monomers obtained can be epoxidized.

In view of the prior art it is now an object of the present invention to provide monomers which can be processed to polymers having outstanding properties. These properties include more particularly features which become apparent through coating materials and coatings which are obtainable from the coating materials.

More particularly the monomers ought to be able to be processed to dispersions and to polymers, emulsion polymers for example, which have a very low residual monomer content.

Additionally, therefore, it was an object of the present invention to provide a coating material which has a particularly long storage life and durability. The intention, furthermore, was that the hardness of the coatings obtainable from the coating materials should be able to be varied over a wide range. More particularly there was an intention that particularly hard, scratch-resistant coatings should be obtainable.

A further object is seen as being that of providing polymers which can be used to obtain coating materials without volatile organic solvents. The coatings obtainable from the coating materials ought to have high weathering stability, more particularly high UV resistance. Furthermore, the films obtainable from the coating materials ought to have a low tack after a short time.

Furthermore, the coatings obtainable from the polymers and monomer mixtures ought to be particularly highly resistant to solvents. This stability ought to be high with respect to a large number of different solvents.

Furthermore, therefore, it was an object of the present invention to specify monomers, polymers and coating materials which are obtainable in a particularly cost-effective way. With regard to the polymers it is noted that they ought to have a small fraction of monomers that are costly and inconvenient to prepare, without detriment to performance.

These objects and others which, although not explicitly stated, are nevertheless readily inferrable or derivable from the circumstances discussed in the introduction are achieved by a monomer having all of the features of claim 1. Judicious modifications of the monomer of the invention are protected in dependent claims. With regard to a monomer mixture, to a polymer, to a coating material and to a process for preparing a monomer mixture, claims 9, 14, 18 and 22 provide achievement of the underlying objects.

The present invention accordingly provides a (meth)acrylate monomer of the general formula (I)

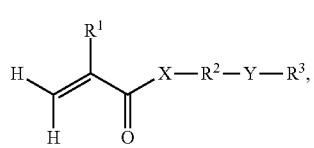

(I)

in which $R^1$ is hydrogen or a methyl group, X is oxygen or a group of the formula NR' in which R' is hydrogen or a radical having 1 to 6 carbon atoms, $R^2$ is an alkylene group having 1 to 22 carbon atoms, Y is oxygen, sulphur or a group of the formula NR", in which R" represents hydrogen or a radical having 1 to 6 carbon atoms, and $R^3$ is an unsaturated radical having 8 carbon atoms and at least two double bonds.

Through the measures according to the invention it is additionally possible to obtain advantages including the following:

The monomer mixtures of the invention can be processed to polymers, coating materials and coatings which have a very low residual monomer content.

The hardness of the coatings obtainable from coating materials of the invention, which are based in turn on the polymers and/or monomer mixtures, can be varied over a wide range. In one preferred modification, in accordance with the invention, it is possible more particularly to obtain particularly hard, scratch-resistant coatings. The coatings obtainable from the coating materials of the present invention exhibit a surprisingly high solvent resistance, which is manifested more particularly in trials with methyl isobutyl ketone (MIBK), ammonia solutions or ethanol. Thus the coatings obtained exhibit an outstanding classification in the context more particularly of trials in accordance with the DIN 68861-1 furniture test.

Coating materials obtainable using the monomer mixtures of the invention do not generally require any volatile organic solvents. Furthermore, the coating materials of the invention exhibit a high level of storage stability, a high durability and a very good storage life. In particular there is virtually no aggregate formed.

The coatings obtainable from the coating materials of the invention exhibit a high level of weathering stability, more particularly a high UV resistance. The films obtainable from the coating materials, furthermore, have a low tack after a short time.

The monomers, monomer mixtures, polymers and coating materials of the invention can be prepared inexpensively on a large scale. With regard to the polymers, it is noted that they may have a relatively low fraction of monomers that are costly and inconvenient to prepare, without detriment to performance. The performance of the polymers is apparent from, among other things, the properties of the coating materials and coatings obtainable therefrom.

The coating materials of the invention are eco-friendly and can be processed and produced safely and without great cost or inconvenience. The coating materials of the invention display a very high shearing stability.

The (meth)acrylate monomer of the invention is of the general formula (I)

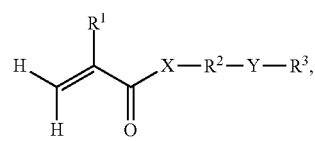

(I)

in which $R^1$ is hydrogen or a methyl group, X is oxygen or a group of the formula NR' in which R' is hydrogen or a radical having 1 to 6 carbon atoms, and $R^2$ is an alkylene group having 1 to 22 carbon atoms, Y is oxygen, sulphur or a group of the formula NR", in which R" represents hydrogen or a radical having 1 to 6 carbon atoms, and $R^3$ is an unsaturated radical having 8 carbon atoms and at least two double bonds.

The expression "radical having 1 to 6 carbon atoms" or "radical having 8 carbon atoms" stands respectively for a group which has 1 to 22 or 8 carbon atoms. It encompasses aromatic and heteroaromatic groups and also alkyl, cycloalkyl, alkoxy, cycloalkoxy, alkenyl, alkanoyl and alkoxycarbonyl groups, plus heteroaliphatic groups. The stated groups may be branched or unbranched. These groups may also have substituents, more particularly halogen atoms or hydroxyl groups.

The radicals R' and R" preferably stand for alkyl groups. The preferred alkyl groups are the methyl, ethyl, propyl, isopropyl, 1-butyl, 2-butyl, 2-methylpropyl and tert-butyl groups.

In formula (I) the radical $R^2$ is an alkylene group having 1 to 22 carbon atoms, preferably having 1 to 10, more preferably having 2 to 6 carbon atoms. In one particular embodiment of the present invention the radical $R^2$ is an alkylene group having 2 to 4, more preferably 2, carbon atoms. The alkylene groups having 1 to 22 carbon atoms include more particularly the methylene, ethylene, propylene, isopropylene, n-butylene, isobutylene, tert-butylene or cyclohexylene group, the ethylene group being particularly preferred.

The radical $R^3$ comprises at least two C—C double bonds which are not part of an aromatic system. Preferably the radical $R^3$ represents a group having precisely 8 carbon atoms which has precisely two double bonds. The radical $R^3$ preferably represents a linear hydrocarbon radical which contains no heteroatoms. In one particular embodiment of the present invention the radical $R^3$ in formula (I) may include a terminal double bond. In a further modification of the present invention, the radical $R^3$ in formula (I) may contain no terminal double bonds. The double bonds present in the radical $R^3$ may preferably be conjugated. In a further preferred embodiment of the present invention the double bonds present in the radical $R^3$ are not conjugated. The preferred radicals $R^3$ which contain at least double bonds include, among others, the octa-2,7-dienyl group, octa-3,7-dienyl group, octa-4,7-dienyl group, octa-5,7-dienyl group, octa-2,4-dienyl group, octa-2,5-dienyl group, octa-2,6-dienyl group, octa-3,5-dienyl group, octa-3,6-dienyl group and octa-4,6-dienyl group.

The preferred monomers of the formula (I) comprise, inter alia, 2-[((2-E)octa-2,7-dienyl)methylamino]ethyl 2-methylprop-2-enoate, 2-[((2-Z)octa-2,7-dienyl)methylamino]ethyl 2-methylprop-2-enoate, 2-[((3-E)octa-3,7-dienyl)methylamino]ethyl 2-methylprop-2-enoate, 2-[((4-Z)octa-4,7-dienyl)methylamino]ethyl 2-methylprop-2-enoate, 2-[((octa-2,6-dienyl)methylamino]ethyl 2-methylprop-2-enoate, 2-[(octa-2,4-dienyl)methylamino]ethyl 2-methylprop-2-enoate, 2-[(octa-3,5-dienyl)methylamino]ethyl 2-methylprop-2-enoate, 2-[((2-E)octa-2,7-dienyl)methylamino]ethyl (meth)acrylamide, 2-[((2-Z)octa-2,7-dienyl)methylamino]ethyl(meth)acrylamide, 2-[((3-E)octa-3,7-dienyl)methylamino]ethyl(meth)acrylamide, 2-[((4-Z)octa-4,7-dienyl)methylamino]ethyl(meth)acrylamide, 2-[((octa-2,6-dienyl)methylamino]ethyl(meth)acrylamide, 2-[((octa-2,4-dienyl)methylamino]ethyl(meth)acrylamide, 2-[((octa-3,5-dienyl)methylamino]ethyl(meth)acrylamide, 2-[((2-E)octa-2,7-dienyl)ethylamino]ethyl 2-methylprop-2-enoate, 2-[((2-Z)octa-2,7-dienyl)ethylamino]ethyl 2-methylprop-2-enoate, 2-[((3-E)octa-3,7-dienyl)ethylamino]ethyl 2-methylprop-2-enoate, 2-[((4-Z)octa-4,7-dienyl)ethylamino]ethyl 2-methylprop-2-enoate, 2-[(octa-2,6-dienyl)ethylamino]ethyl 2-methylprop-2-enoate, 2-[(octa-2,4-dienyl)ethylamino]ethyl 2-methylprop-2-enoate, 2-[(octa-3,5-dienyl)ethylamino]ethyl 2-methylprop-2-enoate, 2-[((2-E)octa-2,7-dienyl)methylamino]ethyl prop-2-enoate, 2-[((2-Z)octa-2,7-dienyl)methylamino]ethyl prop-2-enoate, 2-[((3-E)octa-3,7-dienyl)methylamino]ethyl prop-2-enoate, 2-[((4-Z)octa-4,7-dienyl)methylamino]ethyl prop-2-enoate, 2-[(octa-2,6-dienyl)methylamino]ethyl prop-2-enoate, 2-[(octa-2,4-dienyl)methylamino]ethyl prop-2-enoate, 2-[(octa-3,5-dienyl)methylamino]ethyl prop-2-enoate, 2-((2-E)octa-2,7-dienyloxy)ethyl 2-methylprop-2-enoate, 2-((2-Z)octa-2,7-dienyloxy)ethyl 2-methylprop-2-enoate, 2-((3-E)octa-3,7-dienyloxy)ethyl 2-methylprop-2-enoate, 2-((4-Z)octa-4,7-dienyloxy)ethyl 2-methylprop-2-enoate, 2-(octa-2,6-dienyloxy)ethyl 2-methylprop-2-enoate, 2-(octa-2,4-dienyloxy)ethyl 2-methylprop-2-enoate, 2-(octa-3,5-dienyloxy)ethyl 2-methylprop-2-enoate, 2-((2-E)octa-2,7-dienyloxy)ethyl prop-2-enoate, 2-((2-Z)octa-2,7-dienyloxy)ethyl prop-2-enoate, 2-((3-E)octa-3,7-dienyloxy)ethyl prop-2-enoate, 2-((4-Z)octa-4,7-dienyloxy)ethyl prop-2-enoate, 2-(octa-2,6-dienyloxy)ethyl prop-2-enoate, 2-(octa-2,4-dienyloxy)ethyl prop-2-enoate and 2-(octa-3,5-dienyloxy)ethyl prop-2-enoate.

The (meth)acrylate monomers of formula (I) may be used individually or as a mixture.

In one particular embodiment of the present invention, the monomers of the formula (I) may have an iodine number in the range from 100 to 400 g iodine/100 g, more preferably in the range from 250 to 350 g iodine/100 g.

The (meth)acrylate monomers of the formula (I) set out above can be obtained more particularly by processes in which methacrylic acid, acrylic acid or a mixture thereof, also referred to below for short as (meth)acrylic acid, or a (meth) acrylate, more particularly methyl (meth)acrylate or ethyl (meth)acrylate, is reacted with an alcohol and/or with an amine. Transesterifications of alcohols with (meth)acrylates or the preparation of (meth)acrylamides are set out, moreover, in CN 1355161, DE 21 29 425, filed on 14 Jun. 1971 at the German Patent Office with the application number P 2129425.7, DE 34 23 443 filed on 26 Jun. 1984 at the German Patent Office with the application number P 3423443.8, EP-A-0 534 666 filed on 16 Sep. 1992 at the European Patent Office with the application number EP 92308426.3, or DE 34 30 446 filed on 18 Aug. 1984 at the German Patent Office with the application number P 3430446.0, the reaction conditions described in these publications and also the catalysts etc. set out therein being incorporated for purposes of disclosure into the present specification. Furthermore, these reactions are described in "Synthesis of Acrylic Esters by Transesterification", J. Haken, 1967.

The reactant to be reacted with the (meth)acrylic acid or the (meth)acrylate may advantageously be of the formula (II)

$$H—X—R^2—Y—R^3 \quad (II),$$

in which X is oxygen or a group of the formula NR' in which R' is hydrogen or a radical having 1 to 6 carbon atoms, $R^2$ is an alkylene group having 1 to 22 carbon atoms, Y is oxygen, sulphur or a group of the formula NR" in which R" is hydrogen or a radical having 1 to 6 carbon atoms, and $R^3$ is an at least doubly unsaturated radical having 8 carbon atoms.

With regard to the definition of preferred radicals R', R", $R^2$, Y and $R^3$, reference is made to the description of the formula (I).

The preferred reactants of formula (II) include (methyl (octa-2,7-dienyl)amino)ethanol, (ethyl(octa-2,7-dienyl) amino)ethanol, 2-octa-2,7-dienyloxyethanol, (methyl(octa-2,7-dienyl)amino)ethylamine, (methyl(octa-3,7-dienyl) amino)ethanol, (ethyl(octa-3,7-dienyl)amino)ethanol, 2-octa-3,7-dienyloxyethanol, (methyl(octa-3,7-dienyl) amino)ethylamine, (methyl(octa-4,7-dienyl)amino)ethanol, (ethyl(octa-4,7-dienyl)amino)ethanol, 2-octa-4,7-dienyloxyethanol, (methyl(octa-4,7-dienyl)amino)ethylamine, (methyl (octa-5,7-dienyl)amino)ethanol, (ethyl(octa-5,7-dienyl) amino)ethanol, 2-octa-5,7-dienyloxyethanol, (methyl(octa- 5,7-dienyl)amino)ethylamine, (methyl(octa-2,6-dienyl)amino)ethanol, (ethyl(octa-2,6-dienyl)amino)ethanol, 2-octa-2,6-dienyloxyethanol, (methyl(octa-2,6-dienyl)amino)ethylamine, (methyl(octa-2,5-dienyl)amino)ethanol, (ethyl(octa-2,5-dienyl)amino)ethanol, 2-octa-2,5-dienyloxyethanol, (methyl(octa-2,5-dienyl)amino)ethylamine, (methyl(octa-2,4-dienyl)amino)ethanol, (ethyl(octa-2,4-dienyl)amino)ethanol, 2-octa-2,4-dienyloxyethanol, (methyl(octa-2,4-dienyl)amino)ethylamine, (methyl(octa-3,6-dienyl)amino)ethanol, (ethyl(octa-3,6-dienyl)amino)ethanol, 2-octa-3,6-dienyloxyethanol, (methyl(octa-3,6-dienyl)amino)ethylamine, (methyl(octa-3,5-dienyl)amino)ethanol, (ethyl(octa-3,5-dienyl)amino)ethanol, 2-octa-3,5-dienyloxyethanol, (methyl(octa-3,5-dienyl)amino)ethylamine, (methyl(octa-4,6-dienyl)amino)ethanol, (ethyl(octa-4,6-dienyl)amino)ethanol, 2-octa-4,6-dienyloxyethanol and (methyl(octa-4,6-dienyl)amino)ethylamine. The reactants of formula (II) can be used individually or as a mixture.

The reactants of formula (II) can be obtained by methods including known methods of the telomerization of 1,3-butadiene. The term "telomerization" here denotes the reaction of compounds having conjugated double bonds in the presence of nucleophiles. The processes set out in publications WO 2004/002931, filed on 17 Jun. 2003 at the European Patent Office with the application number PCT/EP2003/006356, WO 03/031379, filed on 1 Oct. 2002 with the application number PCT/EP2002/10971, and WO 02/100803, filed on 4 May 2002 with the application number PCT/EP2002/04909, more particularly the catalysts used for the reaction and the reaction conditions, such as pressure and temperature, for example, are incorporated for purposes of disclosure into the present specification.

The telomerization of 1,3-butadiene may take place preferably using metal compounds which comprise metals of groups 8 to 10 of the periodic table of the elements as catalysts, it being possible with particular preference to use palladium compounds, more particularly palladium-carbene complexes, which are set out in greater detail in the publications listed above.

The nucleophiles used may more particularly be dialcohols, such as ethylene glycol, 1,2-propanediol and 1,3-propanediol; diamines, such as ethylenediamine, N-methylethylenediamine, N,N'-dimethylethylenediamine or hexamethylenediamine; or amino alkanols, such as aminoethanol, N-methylaminoethanol, N-ethylaminoethanol, aminopropanol, N-methylaminopropanol or N-ethylaminopropanol.

The temperature at which the telomerization reaction is performed is between 10 and 180° C., preferably between 30 and 120° C., more preferably between 40 and 100° C. The reaction pressure is 1 to 300 bar, preferably 1 to 120 bar, more preferably 1 to 64 bar and very preferably 1 to 20 bar.

The preparation of isomers of compounds which have an octa-2,7-dienyl group can be accomplished by isomerizing the double bonds which are present in the compounds with an octa-2,7-dienyl group.

The monomer set out above of the formula (I) can be used with advantage in a monomer mixture which comprises one or more monomers which are copolymerizable with the monomer of formula (I).

Advantages which are not obvious per se to a person skilled in the art can be achieved through a monomer mixture which comprises at least 2%, preferably at least 5% by weight and more preferably at least 10% by weight of monomers of the formula (I), based on the total weight of the monomer mixture.

Besides at least one (meth)acrylate monomer of formula (I), the monomer mixture comprises at least one further monomer which is copolymerizable. These copolymerizable monomers include monomers having an acid group, monomers A comprising ester groups and different from the monomers of the formula I, and styrene monomers.

Monomers containing acid groups are compounds which can be copolymerized preferably free-radically with the (meth)acrylate monomers of formula (I) set out above. They include, for example, monomers having a sulphonic acid group, such as vinylsulphonic acid, for example; monomers having a phosphonic acid group, such as vinylphosphonic acid, for example; and unsaturated carboxylic acids, such as methacrylic acid, acrylic acid, fumaric acid and maleic acid, for example. Methacrylic acid and acrylic acid are particularly preferred. The monomers containing acid groups can be used individually or as a mixture of two, three or more monomers containing acid groups.

The preferred monomers A comprising ester groups include, in particular, (meth)acrylates which differ from the monomers of formula (I), and also fumarates, maleates and/or vinyl acetate. The expression (meth)acrylates encompasses methacrylates and acrylates and also mixtures of both. These monomers are widely known.

These include, more particularly, (meth)acrylates having 1 to 6 carbon atoms in the alkyl radical and deriving from saturated alcohols, such as methyl (meth)acrylate, ethyl (meth)acrylate, n-propyl (meth)acrylate, isopropyl (meth)acrylate, n-butyl (meth)acrylate, tert-butyl (meth)acrylate and pentyl (meth)acrylate, hexyl (meth)acrylate; cycloalkyl (meth)acrylates, such as cyclopentyl (meth)acrylate, cyclohexyl (meth)acrylate; and (meth)acrylates deriving from unsaturated alcohols, such as 2-propynyl (meth)acrylate, allyl (meth)acrylate and vinyl (meth)acrylate.

Particular preference is given to using mixtures, to prepare polymers comprising methacrylates and acrylates. Thus it is possible more particularly to use mixtures of methyl methacrylate and acrylates having 2 to 6 carbons, such as ethyl acrylate, butyl acrylate and hexyl acrylate.

These comonomers further include, for example, (meth)acrylates having at least 7 carbon atoms in the alkyl radical and deriving from saturated alcohols, such as, for example, 2-ethylhexyl (meth)acrylate, heptyl (meth)acrylate, 2-tert-butylheptyl (meth)acrylate, octyl (meth)acrylate, 3-isopropylheptyl (meth)acrylate, nonyl (meth)acrylate, decyl (meth)acrylate, undecyl (meth)acrylate, 5-methylundecyl (meth)acrylate, dodecyl (meth)acrylate, 2-methyldodecyl (meth)acrylate, tridecyl (meth)acrylate, 5-methyltridecyl (meth)acrylate, tetradecyl (meth)acrylate, pentadecyl (meth)acrylate, hexadecyl (meth)acrylate, 2-methylhexadecyl (meth)acrylate, heptadecyl (meth)acrylate, 5-isopropylheptadecyl (meth)acrylate, 4-tert-butyloctadecyl (meth)acrylate, 5-ethyloctadecyl (meth)acrylate, 3-isopropyloctadecyl (meth)acrylate, octadecyl (meth)acrylate, nonadecyl (meth)acrylate, eicosyl (meth)acrylate, cetyleicosyl (meth)acrylate, stearyleicosyl (meth)acrylate, docosyl (meth)acrylate and/or eicosyltetratriacontyl (meth)acrylate; cycloalkyl (meth)acrylates, such as 3-vinylcyclohexyl (meth)acrylate, bornyl (meth)acrylate, cycloalkyl (meth)acrylates, such as 2,4,5-tri-t-butyl-3-vinylcyclohexyl (meth)acrylate, 2,3,4,5-tetra-t-butylcyclohexyl (meth)acrylate; heterocyclic (meth)acrylates, such as 2-(1-imidazolyl)ethyl (meth)acrylate, 2-(4-morpholinyl)ethyl (meth)acrylate and 1-(2-methacryloyloxyethyl)-2-pyrrolidone; nitriles of (meth)acrylic acid and other nitrogen-containing methacrylates, such as N-(methacryloyloxyethyl)diisobutylketimine, N-(methacryloyloxyethyl)dihexadecylketimine, methacryloylamidoacetonitrile, 2-methacryloyloxyethylmethylcyanamide, cyanomethyl methacrylate; aryl (meth)acrylates, such as benzyl (meth)acrylate or phenyl (meth)acrylate, it being possible for each of the aryl radicals to be unsubstituted or to be substituted up to four times; (meth)acrylates which contain two or more (meth)acrylic groups, glycol di(meth)acrylates, such as ethylene glycol di(meth)acrylate, diethylene glycol di(meth)acrylate, triethylene glycol di(meth)acrylate, tetra- and polyethylene glycol di(meth)acrylate, 1,3-butanediol (meth)acrylate, 1,4-butanediol (meth)acrylate, 1,6-hexanediol di(meth)acrylate, glycerol di(meth)acrylate; dimethacrylates of ethoxylated bisphenol A; (meth)acrylates having three or more double bonds, such as glycerol tri(meth)acrylate, trimethylolpropane tri(meth)acrylate, pentaerythritol tetra(meth)acrylate and dipentaerythritol penta(meth)acrylate; (meth)acrylates which derive from unsaturated fatty acids, fatty alcohols and fatty acid amides, such as heptadecenyloyloxy-2-ethyl(meth)acrylamide, heptadecane-dien-yloyloxy-2-ethyl(meth)acrylamide, heptadecan-trien-yloyloxy-2-ethyl(meth)acrylamide, heptadecenyloyloxy-2-ethyl(meth)acrylamide, (meth) acryloyloxy-2-ethyl-palmitoleamide, (meth)acryloyloxy-2-ethyloleamide, (meth)acryloyloxy-2-ethyl-icosenamide, (meth)acryloyloxy-2-ethyl-cetoleamide, (meth)acryloyloxy-2-ethyl-erucamide, (meth)acryloyloxy-2-ethyl-linoleamide, (meth)acryloyloxy-2-ethyl-linolenamide, (meth)acryloyloxy-2-propyl-palmitoleamide, (meth)acryloyloxy-2-propyloleamide, (meth)acryloyloxy-2-propylicosenamide, (meth)acryloyloxy-2-propylcetoleamide, (meth)acryloyloxy-2-propylerucamide, (meth)acryloyloxy-2-propyllinoleamide, and (meth)acryloyloxy-2-propyllinolenamide; (meth)acryloyloxy-2-hydroxypropyl-linoleic ester, (meth)acryloyloxy-2-hydroxypropyl-linolenic ester and (meth)acryloyloxy-2-hydroxypropyloleic ester; octadecan-dien-yl (meth)acrylate, octadecan-trien-yl (meth)acrylate, hexadecenyl (meth)acrylate, octadecenyl (meth)acrylate and hexadecan-dien-yl (meth)acrylate; and (meth)acrylates deriving from saturated fatty acid amides, such as pentadecyloyloxy-2-ethyl(meth)acrylamide, heptadecyloyloxy-2-ethyl(meth)acrylamide, (meth)acryloyloxy-2-ethyllauramide, (meth)acryloyloxy-2-ethylmyristamide, (meth)acryloyloxy-2-ethylpalmitamide, (meth)acryloyloxy-2-ethylstearamide, (meth)acryloyloxy-2-propyllauramide, (meth)acryloyloxy-2-propylmyristamide, (meth)acryloyloxy-2-propylpalmitamide and (meth)acryloyloxy-2-propylstearamide.

The monomers A comprising ester groups further include vinyl esters, such as vinyl acetate;
maleic acid derivatives, such as, for example, maleic anhydride, esters of maleic acid, for example dimethyl maleate, methylmaleic anhydride; and fumaric acid derivatives, such as dimethyl fumarate.

A further preferred group of comonomers are styrene monomers, such as, for example, styrene, substituted styrenes having an alkyl substituent in the side chain, such as, for example, α-methylstyrene and α—ethylstyrene, substituted styrenes having an alkyl substituent on the ring, such as vinyltoluene and p-methylstyrene, and halogenated styrenes, such as monochlorostyrenes, dichlorostyrenes, tribromostyrenes and tetrabromostyrenes, for example.

Besides the monomers set out above it is possible for polymers of the invention obtained by the polymerization of monomer mixtures to contain further monomers. These include, for example, heterocyclic vinyl compounds, such as 2-vinylpyridine, 3-vinylpyridine, 2-methyl-5-vinylpyridine, 3-ethyl-4-vinylpyridine, 2,3-dimethyl-5-vinylpyridine, vinylpyrimidine, vinylpiperidine, 9-vinylcarbazole, 3-vinylcarbazole, 4-vinylcarbazole, 1-vinylimidazole, 2-methyl-1-vinylimidazole, N-vinylpyrrolidone, 2-vinylpyrrolidone, N-vinylpyrrolidine, 3-vinylpyrrolidine, N-vinylcaprolactam, N-vinylbutyrolactam, vinyloxolane, vinylfuran, vinylthiophene, vinylthiolane, vinylthiazoles and hydrogenated vinylthiazoles, vinyloxazoles and hydrogenated vinyloxazoles;
maleimide, methylmaleimide;
vinyl ethers and isoprenyl ethers; and
vinyl halides, such as vinyl chloride, vinyl fluoride, vinylidene chloride and vinylidene fluoride, for example.

Preferred monomer mixtures of the present invention comprise
0.1% to 90%, preferably 0.5% to 30%, by weight of (meth)acrylate monomer of formula (I);
10% to 95%, preferably 40% to 90%, by weight of monomers with ester groups A;
0% to 20%, preferably 1% to 8%, more particularly 1%-3%, by weight of monomer having an acid group,
0% to 70%, preferably 0% to 50%, more particularly 0%-30%, by weight of styrene monomers, and
0% to 50%, preferably 0% to 30%, by weight of further comonomers, the amounts being based in each case on the total weight of the monomers.

Mixtures with a high fraction of (meth)acrylate monomer of formula (I) lead generally to polymers or coating materials from which particularly weathering-stable, solvent-resistant and hard coatings are obtained. These mixtures comprise preferably 10% to 90%, preferably 15% to 40%, by weight of (meth)acrylate monomer of formula (I);
10% to 90%, preferably 40% to 85%, by weight of monomers with ester groups A;
0% to 10%, preferably 1% to 8%, by weight of monomer having an acid group,
0% to 50%, preferably 0% to 30%, by weight of styrene monomers, and
0% to 50%, preferably 0% to 30%, by weight of further comonomers, the amounts being based in each case on the total weight of the monomers.

The present invention, moreover, provides coating materials which can be prepared at particularly favourable cost, since they can have a relatively small fraction of expensive monomers, without adversely affecting the properties of the coatings obtainable from the polymers or coating materials. These mixtures comprise preferably
0.1% to 20%, preferably 5% to 10%, by weight of (meth)acrylate monomer of formula (I);
30% to 95%, preferably 40% to 90%, by weight of monomers with ester groups A;
0% to 10%, preferably 1% to 8%, more particularly 1%-3%, by weight of monomer having an acid group,
0% to 50%, preferably 0% to 30%, by weight of styrene monomers, and
0% to 50%, preferably 0% to 30%, by weight of further comonomers, the amounts being based in each case on the total weight of the monomers.

The (meth)acrylate monomers of formula (I) and monomer mixtures of the invention serve in particular for preparing or for modifying polymers. The polymerization can take place in any known way. Such ways include, in particular, free-radical, cationic or anionic polymerization, in which context it is also possible to employ variants of these polymerization processes, such as, for example, ATRP (=Atom Transfer Radical Polymerization), NMP processes (Nitroxide Mediated Polymerization) or RAFT (=Reversible Addition Fragmentation chain Transfer).

The polymers obtainable by these means are new and therefore likewise provided by the present invention. The polymers of the invention comprise at least one unit derived from a (meth)acrylate monomer of the general formula (I). As already described, the monomers of the invention can be reacted by free-radical polymerization. Therefore the term "unit" arises from the reaction of a double bond, with two covalent bonds being constructed. Typically these units are also referred to as repeating units, if there are two or more of these units present in a polymer.

The aforementioned monomers or monomer mixtures can be reacted, for example, by solution polymerizations, bulk polymerizations or emulsion polymerizations, it being possible to achieve surprising advantages by means of a free-radical emulsion polymerization.

Methods of emulsion polymerization are set out in sources including Ullmann's Encyclopedia of Industrial Chemistry, Fifth Edition. The general approach for this is to prepare an aqueous phase which as well as water may include typical additives, more particularly emulsifiers and protective colloids for stabilizing the emulsion.

This aqueous phase is then admixed with monomers, and polymerization is carried out in the aqueous phase. When preparing homogeneous polymer particles, it is possible here to add a monomer mixture batchwise or continuously over a time interval.

The emulsion polymerization can be implemented for example as a miniemulsion or as a microemulsion, and these are set out in more detail in Chemistry and Technology of Emulsion Polymerisation, A. M. van Herk (editor), Blackwell Publishing, Oxford 2005 and J. O'Donnell, E. W. Kaler, Macromolecular Rapid Communications 2007, 28(14), 1445-1454. A miniemulsion is usually characterized by the use of costabilizers or swelling agents, and often long-chain alkanes or alkanols are used. The droplet size in the case of miniemulsions is preferably in the range from 0.05 to 20 μm. The droplet size in the case of microemulsions is situated preferably in the range below 1 μm, allowing particles to be obtained with a size below 50 nm. In the case of microemulsions use is often made of additional surfactants, examples being hexanol or similar compounds.

The dispersing of the monomer-containing phase in the aqueous phase can take place using known agents. These include, more particularly, mechanical methods and also the application of ultrasound.

In the preparation of homogeneous emulsion polymers it is possible with preference to use a monomer mixture which comprises 5% to 50%, more preferably 10% to 40%, by weight of (meth)acrylate monomer of formula (I).

When preparing core-shell polymers it is possible to change the composition of the monomer mixture in steps, polymerization preferably taking place, before the composition is changed, to a conversion of at least 80% by weight, more preferably at least 95% by weight, based in each case on the total weight of the monomer mixture used. A core-shell polymer here is a polymer which has been prepared by a two-stage or multi-stage emulsion polymerization, without the core-shell construction having been shown by means, for example, of electron microscopy. The progress of the polymerization reaction in each step can be monitored in a known way, such as by gravimetry or gas chromatography, for example.

The monomer composition for preparing the core comprises preferably 50% to 100% by weight of (meth)acrylates, particular preference being given to the use of a mixture of acrylates and methacrylates. After the core has been prepared, it is possible to graft or to polymerize onto the core, preferably, a monomer mixture which comprises 10% to 50%, more preferably 15% to 40%, by weight of (meth)acrylate monomer of formula (I).

The emulsion polymerization is conducted preferably at a temperature in the range from 0 to 120° C., more preferably in the range from 30 to 100° C. Polymerization temperatures which have proved to be especially favourable in this context are temperatures in the range from greater than 60 to less than 90° C., judiciously in the range from greater than 70 to less than 85° C., preferably in the range from greater than 75 to less than 85° C.

The polymerization is initiated with the initiators that are customary for emulsion polymerization. Suitable organic initiators are, for example, hydroperoxides such as tert-butyl hydroperoxide or cumene hydroperoxide. Suitable inorganic initiators are hydrogen peroxide and also the alkali metal salts and the ammonium salts of peroxodisulphuric acid, more particularly ammonium, sodium and potassium peroxodisulphate. Suitable redox initiator systems are, for example, combinations of tertiary amines with peroxides or sodium disulphite and alkali metal salts and the ammonium salts of peroxodisulphuric acid, more particularly sodium and potassium peroxodisulphate. Further details can be taken from the technical literature, more particularly H. Rauch-Puntigam, Th. Völker, "Acryl- and Methacrylverbindungen", Springer, Heidelberg, 1967 or Kirk-Othmer, Encyclopedia of Chemical Technology, Vol. 1, pages 386ff., J. Wiley, New York, 1978. Particular preference in the context of the present invention is given to the use of organic and/or inorganic initiators.

The stated initiators may be used both individually and in a mixture. They are preferably used in an amount of 0.05% to 3.0% by weight, based on the total weight of the monomers of the respective stage. It is also possible with preference to carry out the polymerization with a mixture of different polymerization initiators having different half-lives, in order to keep the flow of free radicals constant over the course of the polymerization and also at different polymerization temperatures.

Stabilization of the batch is accomplished preferably by means of emulsifiers and/or protective colloids. The emulsion is preferably stabilized by emulsifiers, in order to obtain a low dispersion viscosity. The total amount of emulsifier is preferably 0.1% to 15% by weight, more particularly 1% to 10% by weight and more preferably 2% to 5% by weight, based on the total weight of the monomers used. In accordance with one particular aspect of the present invention it is possible to add a portion of the emulsifiers during the polymerization.

Particularly suitable emulsifiers are anionic or nonionic emulsifiers or mixtures thereof, more particularly alkyl sulphates, preferably those having 8 to 18 carbon atoms in the alkyl radical, alkyl and alkylaryl ether sulphates having 8 to 18 carbon atoms in the alkyl radical and 1 to 50 ethylene oxide units;

sulphonates, preferably alkylsulphonates having 8 to 18 carbon atoms in the alkyl radical, alkylarylsulphonates having 8 to 18 carbon atoms in the alkyl radical, esters and monoesters of sulphosuccinic acid with monohydric alcohols or alkylphenols having 4 to 15 carbon atoms in the alkyl radical; where appropriate these alcohols or alkylphenols may also have been ethoxylated with 1 to 40 ethylene oxide units;

phosphoric acid partial esters and their alkali metal and ammonium salts, preferably alkyl and alkylaryl phosphates having 8 to 20 carbon atoms in the alkyl or alkylaryl radical and 1 to 5 ethylene oxide units;

alkyl polyglycol ethers, preferably having 8 to 20 carbon atoms in the alkyl radical and 8 to 40 ethylene oxide units;

alkylaryl polyglycol ethers, preferably having 8 to 20 carbon atoms in the alkyl or alkylaryl radical and 8 to 40 ethylene oxide units;

ethylene oxide/propylene oxide copolymers, preferably block copolymers, favourably having 8 to 40 ethylene and/or propylene oxide units.

The particularly preferred anionic emulsifiers include, more particularly, fatty alcohol ether sulphates, diisooctyl sulphosuccinate, lauryl sulphate, C15-paraffinsulphonate, it being possible to use these compounds generally in the form of the alkali metal salt, more particularly the sodium salt. These compounds may be obtained commercially, more particularly, under the commercial designations Disponil® FES 32, Aerosol® OT 75, Texapon® K1296 and Statexan® K1 from the companies Cognis GmbH, Cytec Industries, Inc. and Bayer AG.

Judicious nonionic emulsifiers include tert-octylphenol ethoxylate with 30 ethylene oxide units and fatty alcohol polyethylene glycol ethers which have preferably 8 to 20 carbon atoms in the alkyl radical and 8 to 40 ethylene oxide units. These emulsifiers are available commercially under the commercial designations Triton® X 305 (Fluka), Tergitol® 15-S-7 (Sigma-Aldrich Co.), Marlipal® 1618/25 (Sasol Germany) and Marlipal® O 13/400 (Sasol Germany).

With preference it is possible to use mixtures of anionic emulsifier and nonionic emulsifier. The weight ratio of anionic emulsifier to nonionic emulsifier can judiciously be in the range from 20:1 to 1:20, preferably 2:1 to 1:10 and more preferably 1:1 to 1:5. Mixtures which have proven to be especially appropriate are those comprising a sulphate, more particularly a fatty alcohol ether sulphate, a lauryl sulphate, or a sulphonate, more particularly a diisooctyl sulphosuccinate or a paraffin-sulphonate, as anionic emulsifier, and an alkylphenol ethoxylate or a fatty alcohol polyethylene glycol ether having in each case preferably 8 to 20 carbon atoms in the alkyl radical and 8 to 40 ethylene oxide units as nonionic emulsifier.

Where appropriate the emulsifiers can also be used in a mixture with protective colloids. Suitable protective colloids include partially hydrolysed polyvinyl acetates, polyvinylpyrrolidones, carboxymethyl, methyl, hydroxyethyl and hydroxypropyl cellulose, starches, proteins, poly(meth) acrylic acid, poly(meth)acrylamide, polyvinylsulphonic acids, melamine-formaldehyde sulphonates, naphthalene-formaldehyde sulphonates, styrene-maleic acid and vinyl ether-maleic acid copolymers. If protective colloids are used they are used preferably in an amount of 0.01% to 1.0% by weight, based on the total amount of the monomers. The protective colloids may be included in the initial charge before the start of the polymerization, or metered in. The initiator may be included in the initial charge or metered in. It is also possible, furthermore, to include a portion of the initiator in the initial charge and to meter in the remainder.

The polymerization is preferably started by heating the batch to the polymerization temperature and including the initiator in the initial charge and/or adding it as a metered feed, preferably in aqueous solution. Some of the monomers may be included in the initial charge to the reactor, and the remainder metered in over a defined period of time. Generally it is advantageous to polymerize the portion of the monomers that has been included in the initial charge to the reactor, and only then to begin the feed. As an alternative to including a defined amount of monomer in the initial charge, the feed may be interrupted for a number of minutes after, for example 1%-5% of the monomers have been metered in. The metered feeds of emulsifier and monomers may be implemented separately or, preferably, as a mixture, more particularly as an emulsion in water.

Preferred emulsion polymers with a high fraction of polymers which are insoluble in THF may be obtained in the manner set out above, the reaction parameters for obtaining a high molecular weight being known. Thus in this case it is possible in particular to do without the use of molecular weight regulators. Polymers, particularly emulsion polymers with a high molecular weight, give rise to paint and varnish films which are particularly hard and solvent-resistant.

Paints and varnishes which have particularly good and simple processing qualities may also contain polymers with a relatively low molecular weight, the solvent resistance and the hardness of these coatings attaining a relatively high level. These polymers with a particularly good processing quality may preferably have a molecular weight below 250 000 g/mol, preferably below 150 000 g/mol and more preferably below 100 000 g/mol. The molecular weight can be determined by means of gel permeation chromatography (GPC) against a PMMA standard.

Polymers, especially emulsion polymers, with a low molecular weight can be obtained by the addition of molecular weight regulators to the reaction mixture before or during the polymerization. For this purpose it is possible to use sulphur-free molecular weight regulators and/or sulphur-containing molecular weight regulators.

The sulphur-free molecular weight regulators include, for example—without wishing to impose any restriction— dimeric α-methylstyrene (2,4-diphenyl-4-methyl-1-pentene), enol ethers of aliphatic and/or cycloaliphatic aldehydes, terpenes, β-terpinene, terpinolene, 1,4-cyclohexadiene, 1,4-dihydronaphthalene, 1,4,5,8-tetrahydronaphthalene, 2,5-dihydrofuran, 2,5-dimethylfuran and/or 3,6-dihydro-2H-pyran, preference being given to dimeric α-methylstyrene.

As sulphur-containing molecular weight regulators it is possible with preference to use mercapto compounds, dialkyl sulphides, dialkyl disulphides and/or diaryl sulphides. The following polymerization regulators are named by way of example: di-n-butyl sulphide, di-n-octyl sulphide, diphenyl sulphide, thiodiglycol, ethylthioethanol, diisopropyl disulphide, di-n-butyl disulphide, di-n-hexyl disulphide, diacetyl disulphide, diethanol sulphide, di-tert-butyl trisulphide and dimethyl sulphoxide. Compounds used preferably as molecular weight regulators are mercapto compounds, dialkyl sulphides, dialkyl disulphides and/or diaryl sulphides. Examples of these compounds are ethyl thioglycolate, 2-ethylhexyl thioglycolate, cysteine, 2-mercaptoethanol, 1,3-mercaptopropanol, 3-mercaptopropane-1,2-diol, 1,4-mercaptobutanol, mercaptoacetic acid, 3-mercaptopropionic acid, mercaptosuccinic acid, thioglycerol, thioacetic acid, thiourea and alkyl mercaptans such as n-butyl mercaptan, n-hexyl mercaptan or n-dodecyl mercaptan. Polymerization regulators used with particular preference are mercapto alcohols and mercapto carboxylic acids.

The molecular weight regulators are used preferably in amounts of 0.05% to 10%, more preferably 0.1% to 5%, by weight, based on the monomers used in the polymerization. In the polymerization it is of course also possible to employ mixtures of polymerization regulators.

One of the ways in which the adjustment of the particle radii can be influenced is via the fraction of emulsifiers. The higher this fraction, more particularly at the beginning of the polymerization, the smaller the particles obtained.

The polymers obtainable in accordance with the process described above, especially the emulsion polymers obtainable with preference, represent further subject matter of the present invention.

Preferably the emulsion polymer can have a fraction of 2% to 60%, more preferably 10% to 50% and very preferably 20% to 40%, by weight, based on the weight of the emulsion polymer, which is soluble in tetrahydrofuran (THF) at 20° C. To determine the soluble fraction, a sample of the polymer that has been dried in the absence of oxygen is stored in 200 times the amount of solvent, based on the weight of the sample, at 20° C. for 4 h. In order to ensure the absence of oxygen, the sample, for example, can be dried under nitrogen or under reduced pressure. Subsequently the solution is separated, by filtration for example, from the insoluble fraction. After the solvent has been evaporated the weight of the residue is determined. For example, a 0.5 g sample of an emulsion polymer dried under reduced pressure can be stored in 150 ml of THF for 4 hours.

In accordance with one preferred modification of the present invention an emulsion polymer may exhibit swelling of at least 800%, more preferably at least 1200% and very preferably at least 1300% in tetrahydrofuran (THF) at 20° C. The upper limit on the swelling is not critical per se, the swelling preferably being not more than 5000%, more preferably not more than 3000% and very preferably not more than 2500%. To determine the swelling, a sample of the emulsion polymer that has been dried in the absence of oxygen is stored in 200 times the amount of THF at 20° C. for 4 hours. As a result the sample swells. The swollen sample is separated from the supernatant solvent. Subsequently the solvent is removed from the sample. For example, a major fraction of the solvent can be evaporated at room temperature (20° C.). Solvent residues can be removed in a drying oven (140° C.), generally over the course of 1 hour. From the weight of the solvent absorbed by the sample and the weight of the dry sample the swelling is obtained. Furthermore, the difference in the weight of the sample prior to the swelling experiment and the weight of the dried sample after the swelling experiment produces the soluble fraction of the emulsion polymer.

The particle radius of the emulsion polymers can be within a wide range. Thus, in particular, it is possible to use emulsion polymers having a particle radius in the range from 10 to 500 nm, preferably 10 to 100 nm, particularly preferably 20 to 60 nm. More particularly, particle radii of less than 50 nm may be advantageous for film formation and coating properties. The radius of the particles can be determined by means of PCS (Photon Correlation Spectroscopy), the data given relating to the d50 value (50% of the particles are smaller, 50% are larger). This can be done using, for example, a Beckman Coulter N5 Submicron Particle Size Analyzer.

The glass transition temperature of the polymer of the invention is situated preferably in the range from −30° C. to 70° C., more preferably in the range from −20 to 40° C. and very preferably in the range from 0 to 25° C. The glass transition temperature may be influenced via the nature and the fraction of the monomers used to prepare the polymer. The glass transition temperature, Tg, of the polymer may be determined in a known way by means of Differential Scanning Calorimetry (DSC). Moreover, the glass transition temperature Tg may also be calculated approximately in advance by means of the Fox equation. According to Fox T. G., Bull. Am. Physics Soc. 1, 3, page 123 (1956) it is the case that:

$$\frac{1}{Tg} = \frac{x_1}{Tg_1} + \frac{x_2}{Tg_2} + \ldots + \frac{x_n}{Tg_n}$$

where $x_n$ represents the mass fraction (% by weight/100) of the monomer n and $Tg_n$ identifies the glass transition temperature, in kelvin, of the homopolymer of the monomer n. Further useful information can be found by the skilled person in the Polymer Handbook, 2nd Edition, J. Wiley & Sons, New York (1975), which gives Tg values for the most common homopolymers. The polymer here may have one or more different glass transition temperatures. These figures therefore apply to a segment obtainable by polymerizing at least one (meth)acrylate monomer of formula (I), preferably a monomer mixture of the invention.

For many applications and properties the architecture of the polymer is not critical. The polymers, especially the emulsion polymers, may accordingly comprise random copolymers, gradient copolymers, block copolymers and/or graft copolymers. Block copolymers and gradient copolymers can be obtained, for example, by discontinuously altering the monomer composition during chain propagation. In accordance with one preferred aspect of the present invention the emulsion polymer comprises a random copolymer in which the monomer composition over the polymerization is substantially constant. Since, however, the monomers may have different copolymerization parameters, the precise composition may fluctuate over the polymer chain of the polymer.

The polymer may constitute a homogeneous polymer which, for example, in an aqueous dispersion forms particles having a consistent composition. In this case the polymer, which is preferably an emulsion polymer, may be composed of one or more segments obtainable by polymerizing at least one (meth)acrylate monomer of formula (I), preferably a monomer mixture of the invention.

In accordance with another embodiment the emulsion polymer may constitute a core-shell polymer, which may have one, two, three or more shells. In this case the segment obtainable by polymerizing the monomer mixture of the invention or the (meth)acrylate monomer of formula (I) preferably forms the outermost shell of the core-shell polymer. The shell may be connected to the core or to the inner shells via covalent bonds. Moreover, the shell may also be polymerized onto the core or onto an inner shell. In this embodiment the segment obtainable by polymerizing the monomer mixture of the invention may in many cases be separated and isolated from the core by means of suitable solvents.

The weight ratio of segment obtainable by polymerizing the monomer mixture of the invention or the (meth)acrylate monomer of formula (I) to core may be situated preferably in the range from 6:1 to 1:6. Where the glass transition temperature of the core is higher than that of the shell, a ratio of 6:1 to 2:1 is particularly preferred; in the opposite case, 1:1 to 1:5 is particularly preferred.

The core may be formed preferably of polymers comprising 50% to 100%, preferably 60% to 90%, by weight of units derived from (meth)acrylates. Preference here is given to esters of (meth)acrylic acid whose alcohol residue comprises preferably 1 to 30 carbon atoms, more preferably 1 to 20 carbon atoms and very preferably 1 to 10 carbon atoms. They include, more particularly, (meth)acrylates deriving from saturated alcohols, such as methyl (meth)acrylate, ethyl (meth)acrylate, n-propyl (meth)acrylate, isopropyl (meth) acrylate, n-butyl (meth)acrylate, tert-butyl (meth)acrylate, pentyl (meth)acrylate and hexyl (meth)acrylate.

In accordance with one particular embodiment of the present invention the core can be prepared using a mixture which comprises methacrylates and acrylates. Thus it is possible more particularly to use mixtures of methyl methacrylate and acrylates having 2 to 6 carbons, such as ethyl acrylate, butyl acrylate and hexyl acrylate.

Furthermore, the polymers of the core may comprise the comonomers set out above. In accordance with one preferred modification the core may be crosslinked. This crosslinking may be achieved through the use of monomers having two, three or more free-radically polymerizable double bonds.

The shell of an emulsion polymer of the present invention that is obtainable by polymerizing a monomer mixture of the invention may comprise preferably 15% to 50% by weight of units derived from (meth)acrylate monomers of formula (I).

In accordance with one particular aspect the core may preferably have a glass transition temperature in the range from −30 to 200° C., more particularly in the range from −20 to 150° C. Particular preference is given to a glass transition temperature >50° C., more particularly >100° C. The shell of the emulsion polymer of the invention, preferably obtainable by polymerizing the monomer mixture of the invention, may preferably have a glass transition temperature in the range from −30° C. to 70° C., more preferably in the range from −20 to 40° C. and very preferably in the range from 0 to 25° C. In accordance with one particular aspect of the present invention the glass transition temperature of the core may be greater than the glass transition temperature of the shell. Judiciously the glass transition temperature of the core may be at least 10° C., preferably at least 20° C., above the glass transition temperature of the shell.

The iodine number of the polymers of the invention is preferably in the range from 1 to 300 g iodine per 100 g polymer, more preferably in the range from 2 to 270 g iodine per 100 g polymer and very preferably 5 to 250 g iodine per 100 g polymer, measured in accordance with DIN 53241-1. The iodine number may also be measured more particularly on the basis of a dispersion of the invention.

Judiciously the polymer may have an acid number in the range from 0 to 50 mg KOH/g, preferably 0.1 to 40 mg KOH/g, more preferably 1 to 20 mg KOH/g and very preferably in the range from 2 to 10 mg KOH/g. The acid number may be determined in accordance with DIN EN ISO 2114 also from a dispersion.

The hydroxyl number of the polymer can be situated preferably in the range from 0 to 200 mg KOH/g, more preferably 1 to 100 mg KOH/g and very preferably in the range from 3 to 50 mg KOH/g. The hydroxyl number may be determined in accordance with DIN EN ISO 4629 also from a dispersion.

The polymers obtainable by polymerizing (meth)acrylate monomers of formula (I) or a monomer mixture of the invention can be isolated. In accordance with one particular embodiment of the present invention, the dispersions obtainable by emulsion polymerization can be employed as they are, as coating materials.

Coating materials which comprise the above polymers or compounds obtainable by reactions with the above (meth)acrylate monomers are likewise provided by the present invention. Coating materials are compositions which are suitable for the coating of substrates. The coating materials of the invention are oxidatively crosslinkable, and so crosslinked films which often have a high solvent resistance, are produced from the coating materials on exposure to oxygen.

Besides the coating materials which comprise above polymers, it is also possible with success to use coating materials which are based on alkyd resins which have been modified with the (meth)acrylate monomers of the invention or the monomer mixtures of the invention. The term "modification" here is to be understood broadly, and so encompasses alkyd resins which contain one or more units, or repeating units, derived from the (meth)acrylate monomers of formula (I). Also embraced by the concept of "modification" are alkyd resins or alkyd resin dispersions which comprise the polymers set out above.

Alkyd resins are well established, the term referring generally to resins obtained by condensing polybasic carboxylic acids and polyhydric alcohols, these compounds generally being modified with long-chain alcohols (fatty alcohols), fatty acids or compounds containing fatty acid, examples being fats or oils (DIN 55945; 1968). Alkyd resins are described for example in Ullmann's Encyclopedia of Industrial Chemistry, 5th edition on CD-ROM. Besides these conventional alkyd resins it is also possible to use resins which have similar properties. These resins are likewise distinguished by a high level of groups derived from long-chain alcohols (fatty alcohols), fatty acids and/or compounds containing fatty acid, examples being fats or oils. These derivatives, however, do not necessarily contain polybasic carboxylic acids, but may instead be obtained, for example, by reaction of polyols with isocyanates. The alkyd resins that can be employed may be diluted or mixed preferably with water.

Preferred polybasic carboxylic acids for preparing the alkyd resins to be used with preference in the dispersion of the invention include dicarboxylic and tricarboxylic acids, such as, for example, phthalic acid, isophthalic acid, 5-(sodiumsulpho)isophthalic acid, terephthalic acid, trimellitic acid, 1,4-cyclohexanedicarboxylic acid, butanedioic acid, maleic acid, fumaric acid, sebacic acid, adipic acid and azelaic acid. These acids can also be used as anhydrides for the preparation. Particular preference is given to using aromatic dicarboxylic acids to prepare the alkyd resins. The fraction of polybasic carboxylic acids is preferably in the range from 2% to 50% by weight, more preferably 5% to 40% by weight, based on the weight of the reactants for preparing the resin that are used in the reaction mixture.

The alkyd resins are additionally prepared using polyhydric alcohols. These alcohols include trimethylolpropane, pentaerythritol, dipentaerythritol, trimethylolethane, neopentylglycol, ethylene glycol, 1,3-butanediol, 1,4-butanediol, 1,6-hexanediol, 1,4-cyclohexyldimethanol, diethylene glycol, triethylene glycol, polyethylene glycol, polytetrahydrofuran, polycaprolactonediol, polycaprolactonetriol, trimethylol monoallyl ether, trimethylol diallyl ether, pentaerythritol triallyl ether, pentaerythritol diallyl ether, pentaerythritol monoallyl ether, 2-ethyl-2-(hydroxymethyl)-1,3-propanediol, 2-methyl-1,3-propanediol, 2,2,4-trimethylpentanediol, 2,2,4-trimethyl-1,3-pentanediol, 2,2'-bis(4-hydroxycyclohexyl)propane (hydrogenated bisphenol A), propylene glycol, dipropylene glycol, polypropylene glycol, glycerol, and sorbitol. Particular preference among these is given to trimethylolethane, trimethylolpropane, pentaerythritol and sorbitol. In one particular aspect preference is given more particularly to alcohols having three or more hydroxyl groups. The fraction of polyhydric alcohols is preferably in the range from 2% to 50% by weight, more preferably 5% to 40% by weight, based on the weight of the reactants for preparing the resin that are used in the reaction mixture.

Furthermore it is possible in particular to use fatty acids to prepare the alkyd resins set out above. In this case use may be made more particularly of saturated and unsaturated fatty acids, particular preference being given to mixtures which comprise unsaturated fatty acids. Preferred fatty acids have 6 to 30, more preferably 10 to 26 and very preferably 12 to 22 carbon atoms. The fraction of fatty acids is preferably in the range from 2% to 90% by weight, more preferably 10% to 70% by weight, based on the weight of the reactants for preparing the resin that are used in the reaction mixture.

The suitable saturated fatty acids include caprylic acid, capric acid, lauric acid, myristic acid, palmitic acid, margaric acid, arachidic acid, behenic acid, lignoceric acid, cerotinic acid, palmitoleic acid and stearic acid.

The preferred unsaturated fatty acids include undecylenoic acid, palmitoleic acid, oleic acid, elaidic acid, vaccenic acid, icosenoic acid, cetoleic acid, erucic acid, nervonic acid, linoleic acid, linolenic acid, arachidonic acid, timnodonic acid, clupanodonic acid and/or cervonic acid.

The fatty acids set out above may also be used, furthermore, in the form of their esters, as for example in the form of triglycerides.

The alkyd resins set out above may, furthermore, contain additional components. Examples of such components include monobasic carboxylic acids, monohydric alcohols or compounds which lead to emulsifying groups in the resins, such as polyethylene oxides, for example. The alkyd resins may further contain hydroxy carboxylic acids, such as 2-, 3- and 4-hydroxybenzoic acid, ricinoleic acid, dihydroxypropionic acid, dihydroxysuccinic acid, dihydroxybenzoic acid, 2,2-dimethylolacetic acid, 2,2-dimethylolpropionic acid, 2,2-dimethylolbutyric acid and 2,2-dimethylolpentanoic acid.

Additionally it is also possible to use modified alkyd resins which have been modified with resins, especially rosin, with styrene polymers, with acrylic polymers, with epoxides, with urethanes, with polyamides and/or with silicones. These modifications are set out in references which include the above-recited patent literature and Ullmann's Encyclopedia of Industrial Chemistry 5th edition on CD-ROM. Through these embodiments it is possible to modify more particularly the initial drying, the adhesive strength, the weathering stability, the storage life, the chemical resistance, the volume curing, the sag resistance of the wet film, and the abrasion resistance.

By way of example it is possible with preference to use alkyd resins which have been modified with polymers obtainable by free-radical polymerization. Resins of this kind are disclosed in publications including U.S. Pat. Nos. 5,538,760, 6,369,135 and DE-A-199 57 161. The resins set out in publication U.S. Pat. No. 5,538,760, filed on 22 May 1995 at the Patent Office of the United States of America (USPTO) with the application number 446,130, are included for purposes of disclosure in the present application. The resins set out in publication U.S. Pat. No. 6,369,135 B1, filed on 13 Aug. 1996 at the Patent Office of the United States of America (USPTO) with the application Ser. No. 08/696,361, are included for purposes of disclosure in the present application. The resins set out in publication DE-A-199 57 161, filed on 27 Nov. 1999 at the German Patent and Trademark Office (DPMA) with the application number DE 19957161.9, are included for purposes of disclosure in the present specification.

According to publications U.S. Pat. Nos. 5,538,760 and 6,369,135, modified alkyd resins can be obtained by methods including the polymerization of a monomer mixture in the presence of an alkyd resin. The weight ratio of monomer mixture to alkyd resin in this case is preferably in the range from 100:1 to 1:4, preferably 5:1 to 1:1.

Particularly judicious are resins including the acrylate-modified alkyd resins described in DE-A-199 57 161. These alkyd resins, in addition to an alkyd core, contain groups obtained by polymerizing (meth)acrylates.

These acrylate-modified alkyd resins can be prepared by—operating in the presence of at least one water-miscible diol—

(1) dispersing in water at least one alkyd resin which, based on its total amount, contains 0.1% to 10% by weight of pendant and/or terminal allyloxy groups, to give dispersion 1, (2) subjecting a mixture of methacrylic acid and at least one further, carboxyl-free olefinically unsaturated monomer to graft copolymerization in dispersion 1, to give dispersion 2, and (3) once or n times, subjecting (3.1) at least one acid-group-free olefinically unsaturated monomer and/or (3.2) at least one mixture of at least one acid-group-containing olefinically unsaturated monomer and at least one acid-group-free olefinically unsaturated monomer to graft copolymerization in the dispersion 2 or 2 to n−1 resulting from the respective previous process step (2) or (2) to (n−1), with the proviso that, in step (3) of the process or in its repetitions (3) to (n), acid groups are incorporated in an amount corresponding in total to not more than 90 mol % of the amount of acid groups incorporated in step (2) of the process.

The aforementioned pendant and/or terminal allyloxy group may be present in the alkyd resin in an amount, based in each case on the alkyd resin, of 0.1% to 10%, preferably 0.2% to 9%, more preferably 0.3% to 8%, very preferably 0.4% to 7%, with very particular preference 0.5% to 6% and in particular 0.6% to 5% by weight. The oxygen atom of the allyloxy group may be part of a urethane group, an ester group or an ether group that connects the allyl radical to the main chain of the alkyd resin.

Examples of suitable compounds for introducing pendant and/or terminal allyloxy groups are allyl alcohol, 2-hydroxyethyl allyl ether, 3-hydroxypropyl allylether, trimethylolpropane monoallyl or diallyl ether, glycerol monoallyl or diallyl ether, pentaerythritol monoallyl, diallyl or triallyl ether, mannitol monoallyl, diallyl, triallyl or tetraallyl ether, allyl esters of dihydroxypropionic, dihydroxysuccinic, dihydroxybenzoic, 2,2-dimethylolacetic, 2,2-dimethylolpropionic, 2,2-dimethylolbutyric or 2,2-dimethylolpentanoic acids, or allylurethane, among which advantage is possessed by trimethylolpropane monoallyl ether. For the modification with acrylates, dispersion 1 can be subjected in a step (2) to graft copolymerization with methacrylic acid and at least one further olefinically unsaturated monomer. The further olefinically unsaturated monomers may, in addition to the olefinically unsaturated double bonds, also contain reactive functional groups, with the exception of carboxyl groups—for example isocyanate-reactive, carbamate-reactive, N-methylol- or N-methylol ether-reactive or alkoxycarbonylamino-reactive groups. It is essential here that these reactive functional groups, under the prevailing reaction conditions and during the subsequent storage of the dispersions of the invention, do not enter into any reactions with the carboxyl groups of the methacrylic acid or with other reactive functional groups that may be present. One example of reactive functional groups which meet these requirements is the hydroxyl group. These monomers are known per se, with examples being set out in DE 199 57 161. They include more particularly hydroxyalkyl esters of acrylic acid, of methacrylic acid or of another alpha,beta-olefinically unsaturated carboxylic acid, esters of acrylic acid, of methacrylic acid, of crotonic acid or of ethacrylic acid with up to 20 carbon atoms in the alkyl radical.

Preference extends to alkyd resins obtainable in accordance with publication U.S. Pat. No. 5,096,959. For the purposes of disclosure, the resins set out in the publication U.S. Pat. No. 5,096,959 B1 filed on 30 Oct. 1990 at the Patent Office of the United States of America (USPTO) with the application number 609,024 are incorporated in the present specification. These alkyd resins are modified with cycloaliphatic polycarboxylic acid, with cyclohexanedicarboxylic and cyclopentanedicarboxylic acids in particular being suitable for the modification.

Additionally it is possible to use alkyd resins which have been modified with polyethylene glycol. A large number of patents describe the preparation of water-emulsifiable alkyd resins by modification with polyethylene glycol (PEG). In the majority of processes about 10% to 30% of PEG is incorporated into the alkyd resin directly by esterification or transesterification (see inter alia U.S. Pat. Nos. 2,634,245; 2,853,459; 3,133,032; 3,223,659; 3,379,548; 3,437,615; 3,437,618; 3,442,835; 3,457,206; 3,639,315; German laid-open specification 14 95 032, or British Patents Nos. 1,038,696 and 1,044,821).

Preferred alkyd resins modified with polyethylene glycol are known from sources including publication EP-A-0 029 145. For the purposes of disclosure, the resins set out in the publication EP-A-0 029 145 filed on 30 Oct. 1980 at the European Patent Office with the application number EP 80106672.1 are incorporated in the present specification. According to that publication it is possible first to react a polyethylene glycol with carboxylic acid containing epoxide groups. The resulting reaction product can then be used in the reaction mixture for preparing the alkyd resin. Preferred polyethylene glycols for modifying the alkyd resins have a number-average molecular weight of 500 to 5000 g/mol, for example.

Particularly preferred polyethylene glycol-modified alkyd resins may additionally be modified with copolymers which are obtainable by polymerizing methacrylic acid, unsaturated fatty acids and vinyl and/or vinylidene compounds.

Additionally judicious are alkyd resins which have been modified with urethane groups. The alkyd resins of this kind are set out in WO 2006/092211 and EP-A-1 533 342, among others.

In one judicious embodiment it is possible to use the urethane alkyd resins that are described in EP-A-1 533 342 and comprise units derived from unsaturated fatty acids A1, aliphatic or aromatic or aromatic-aliphatic monocarboxylic acids A2 that are free from olefinic double bonds, cycloaliphatic dicarboxylic acids A3 or their anhydrides, at least trihydric and preferably at least tetrahydric alcohols A4, and aromatic or aliphatic polyfunctional, especially difunctional, isocyanates A5. The urethane alkyd resin is prepared preferably in a two-stage reaction, with components A1 to A4 being esterified in the first stage, the acid number of the product of the first stage being preferably not more than 10 mg/g, more preferably not more than 5 mg/g. In the second stage the hydroxyl-containing product of the first stage is reacted with the isocyanate A5, with addition of a small amount (up to 1% of the mass of the product of the first stage, preferably up to 0.5% of its mass) of a tertiary amine, in a molecular enlargement reaction. Preferred urethane alkyd resins have a Staudinger index, measured in chloroform at 23° C., of at least 9 cm$^3$/g, preferably at least 11 cm$^3$/g.

For the purposes of disclosure, the resins set out in publication EP-A-1 533 342, filed on 9 Nov. 2004 at the European Patent Office with the application number EP 04026511.8, are included in the present application.

With preference it is possible to use urethane alkyd resins which are obtainable by reacting polyhydric alcohols A', modified fatty acids B', fatty acids C' and polyfunctional isocyanates D'. The modified fatty acids B' can be prepared by reacting unsaturated fatty acids B1' with unsaturated carboxylic acids B2'. These urethane alkyds are known from publications including WO 2006/092211. For the purposes of disclosure, the resins set out in publication WO 2006/092211, filed on 20 Feb. 2006 at the European Patent Office with the application number PCT/EP2006/001503, are included in the present specification. The modified fatty acid B' preferably has an acid number of at least 80 mg/g. With particular preference the increase in acid number as a result of the grafting is in the range from 80 mg/g to 250 mg/g, and very preferably in the range from 100 mg/g to 150 mg/g, the acid number being determinable in accordance with DIN EN ISO 2114. The iodine number of the fatty acids C' used for preparing the urethane alkyd resins is preferably at least 80 g/100 g and preferably at least 120 g/100 g. For preparing the urethane alkyd resin described in WO 2006/092211, in general, first components A', B' and C' are reacted, the condensate preferably having a hydroxy functionality of at least 1.9, more preferably at least 2. Furthermore, the condensate may contain groups derived from polybasic carboxylic acids, especially the above-described dicarboxylic and tricarboxylic acids. This condensate is subsequently reacted with a polyfunctional isocyanate. The preferred polyfunctional isocyanates include, among others, 2,4- and 2,6-tolylene diisocyanate and also the technical mixtures thereof, bis(4-isocyanatophenyl)methane, isophorone diisocyanate, bis(4-isocyanato-cyclohexyl)methane and 1,6-diisocyanatohexane, and the biurets, allophanates and isocyanurates derived therefrom.

Besides the above-described conventional alkyd resins, prepared using, generally, polycarboxylic acids, it is also possible to use further alkyd resins, as has already been set out above. These include in particular alkyd resins which are based on urethanes. These urethane alkyd resins can be obtained for example by reaction of polyhydric alcohols with polyfunctional isocyanates. Preferred urethane resins are known for example from EP-A-1 129 147. They can be obtained, for example, by reaction of amide ester diols with polyols and polyfunctional isocyanates. The amide ester diols for use in accordance with EP-A-1 129 147 can be obtained by reacting vegetable oils with N,N-dialkanolamines.

According to one preferred aspect of the present invention, the alkyd resin may have an iodine number in accordance with DIN 53241 of at least 1 g iodine/100 g, preferably of at least 10 g iodine/100 g, more preferably at least 15 g iodine/100 g. According to one particular aspect of the present invention, the iodine number of the alkyd resin may lie in the range from 2 to 100 g iodine per 100 g alkyd resin, more preferably 15 to 50 g iodine per 100 g alkyd resin. The iodine number may be determined on the basis of a dispersion, in which case the value is based on the solids content.

Judiciously the alkyd resin may have an acid number in the range from 0.1 to 100 mg KOH/g, preferably 1 to 40 mg KOH/g and very preferably in the range from 2 to 10 mg KOH/g. The acid number can be determined in accordance with DIN EN ISO 2114 from a dispersion, in which case the value is based on the solids content.

The alkyd resin may preferably have a hydroxyl number in the range from 0 to 400 mg KOH/g, more preferably 1 to 200 mg KOH/g and very preferably in the range from 3 to 150 mg KOH/g. The hydroxyl number can be determined in accordance with DIN EN ISO 4629 from a dispersion, in which case the value is based on the solids content.

The preparation of the alkyd resins is well established and is accomplished by condensing the above-recited alcohols and acids, it being possible for modification to take place both during this condensation and after this condensation. Reference in this context is made in particular to the literature set out above.

In the coating materials of the invention it is possible to use the above-recited alkyd resins without modification, but together with polymers of the invention. With regard to the modification it is noted that it can be achieved preferably by polymerizing a (meth)acrylate monomer of formula (I) or a monomer mixture of the invention, with useful information concerning the reaction regime being found in publications including EP-A-0 083 137, the alkyd resins and reaction conditions set out in publication EP-A-0 083 137, filed on 21 Dec. 1987 at the European Patent Office with the application number 82201642.4, being incorporated for purposes of disclosure into the present specification.

The coating material preferably comprises only small amounts of environmentally hazardous solvents, with aqueous dispersions representing particularly preferred coating materials. The aqueous dispersions preferably have a solids content in the range from 10% to 70% by weight, more preferably 20% to 60% by weight. The dynamic viscosity of the dispersion is dependent on the solids content and the particle size and may encompass a wide range. Thus in the case of fine-particle dispersions with a high polymer content the dynamic viscosity may in some cases be more than 10 000 mPas. Judiciously the dynamic viscosity is usually in the range from 10 to 4000 mPas, preferably 10 to 1000 mPas and very preferably 10 to 500 mPas, measured in accordance with DIN EN ISO 2555 at 25° C. (Brookfield).

Additionally the aqueous dispersions of the invention may be provided in a known manner with additives or further components for adapting the properties of the coating material to specific requirements. These adjuvants include, more particularly, drying assistants, known as siccatives, and flow improvers, pigments and dyes.

The coating materials of the invention preferably have a minimum film formation temperature of not more than 50° C., with particular preference not more than 35° C. and very particular preference not more than 25° C., a temperature which can be measured in accordance with DIN ISO 2115.

In accordance with one preferred aspect of the present invention it is possible for a coating material of the invention, more particularly an aqueous dispersion, to have an iodine number in accordance with DIN 53241 of at least 1 g iodine/100 g, preferably of at least 10 g iodine/100 g, more preferably of at least 15 g iodine/100 g. In accordance with one particular aspect of the present invention, the iodine number of the aqueous dispersion may be in the range from 2 to 100 g of iodine per 100 g of aqueous dispersion, more preferably 15 to 50 g of iodine per 100 g of aqueous dispersion. The iodine number can be determined on the basis of a dispersion, in which case the value is based on the solids content.

Judiciously the coating material, preferably an aqueous dispersion, may have an acid number in the range 0.1 to 100 mg KOH/g, preferably 1 to 40 mg KOH/g and very preferably in the range from 2 to 10 mg KOH/g. The acid number may be determined in accordance with DIN EN ISO 2114 on the basis of a dispersion, in which case the value is based on the solids content.

The hydroxyl number of a coating material of the invention, more particularly of an aqueous dispersion, may lie preferably in the range from 0 to 400 mg KOH/g, more preferably 1 to 200 mg KOH/g and very preferably in the range from 3 to 150 mg KOH/g. The hydroxyl number may be determined in accordance with DIN EN ISO 4629 on the basis of a dispersion, in which case the value is based on the solids content.

The coating materials of the invention do not require siccatives, although such additives may be included as an optional constituent in the compositions. With particular preference it is possible to add siccatives to the aqueous dispersions. These siccatives include, more particularly, organometallic compounds, examples being metal soaps of transition metals, such as cobalt, manganese, lead and zirconium, for example; alkali metals or alkaline earth metals, such as lithium, potassium and calcium, for example. Examples that may be mentioned include cobalt naphthalate and cobalt acetate. The siccatives can be used individually or as a mixture, in which case particular preference is given more particularly to mixtures which comprise cobalt salts, zirconium salts and lithium salts.

The polymers of the present invention can be used more particularly in coating materials or as an adjuvant. Such materials include, more particularly, paints and varnishes, impregnating compositions, adhesives and/or primer systems. With particular preference the coating materials, especially the aqueous dispersions, can be employed for producing paints, varnishes or impregnating compositions for applications on wood and/or metal.

The coatings obtainable from the coating materials of the invention exhibit high solvent resistance; more particularly, only small fractions are dissolved from the coating by solvents. Preferred coatings exhibit a high resistance, more particularly, to methyl isobutyl ketone (MIBK). Hence the weight loss after treatment with MIBK amounts preferably to not more than 50% by weight, more preferably not more than 35% by weight. The absorption of MIBK amounts preferably to not more than 400% by weight, with particular preference not more than 250% by weight, based on the weight of the coating used. These values are measured at a temperature of approximately 25° C. and over an exposure time of at least 4 hours, the coating subjected to measurement being a fully dried coating. In this case, drying takes place in the presence of oxygen, for example atmospheric air, in order to allow crosslinking to take place.

The coatings obtained from the coating materials of the invention display a high mechanical stability. The pendulum hardness is preferably at least 15 s, more preferably at least 25 s, measured in accordance with DIN ISO 1522.

Besides the emulsion polymers, the dispersions of the invention may also comprise further constituents.

The present invention will be illustrated below with reference to an inventive example and comparative examples, without any intention thereby to restrict the invention.

EXAMPLE 1

Preparation of 2-[((2-E)octa-2,7-dienyl)methylamino]ethyl 2-methylprop-2-enoate

First of all (methyl(octa-2,7-dienyl)amino)ethanol was prepared. This was done by admixing 48 mg of PddvdslMes (1,3-dimesitylimidazol-2-ylidenepalladium(0)-$\eta^2,\eta^2$,-1,1,3,3-tetramethyl-1,3-divinyldisiloxane, $8.1 \times 10^{-5}$ mol) and 351 mg of 1,3-dimesityl-1H-imidazol-3-ium methanesulfonate ($8.7 \times 10^{-4}$ mol) in a 1 l Schlenk flask under argon with 100 ml of MeOH and 185 ml of N-methylaminoethanol (173 g, 2.3 mol). The solution was stirred for half an hour and transferred under argon to a 2 l stainless steel autoclave (Parr Instruments). The autoclave was cooled with dry ice, and 220 g of butadiene (4.1 mol) were condensed in. The autoclave was warmed to room temperature, a pressure of 20 bar being generated with nitrogen. Subsequently it was stirred at 80° C. for 20 hours. After the end of the reaction, the autoclave was cooled, the pressure was let off and the reaction solution was returned to a 1 l Schlenk flask. The product obtained was purified by vacuum distillation, the boiling temperature being approximately 60° C. 349 g (93%) of product were obtained. The product was analysed by means of NMR spectroscopy.

The resulting (methyl(octa-2,7-dienyl)amino)ethanol was subsequently reacted with methyl methacrylate to give 2-[((2-E)octa-2,7-dienyl)methylamino]ethyl-2-methylprop-2-enoate.

For this purpose, 140.0 g (0.76 mol) of (E)-2-(methyl(octa-2,7-dienyl)amino)ethanol, 760.8 g (7.60 mol) of methyl methacrylate, 0.191 g (1000 ppm) of hydroquinone monomethyl ether (HMQE) and 0.191 g (1000 ppm) of phenothiazine were introduced. The batch was then dewatered azeotropically using methyl methacrylate. Then the catalyst (2.80 g of tetraisopropyl titanate in solution in 2.80 g of methyl methacrylate) was added.

The reaction mixture was heated at boiling. The methyl methacrylate/methanol azeotrope was separated off, the overhead temperature climbing in steps to 100° C. After the end of the reaction, the mixture was briefly cooled, the catalyst was precipitated by addition of 20 ml of water, and cooling continued to room temperature with stirring. Following filtration, the excess methyl methacrylate was distilled off on a rotary evaporator.

EXAMPLE 2

Preparation of 2-((2-E)octa-2,7-dienyloxy)ethyl 2-methylprop-2-enoate

First of all 2-octa-2,7-dienyloxyethanol was prepared. This was done by admixing 33 mg of PddvdslMes (1,3-dimesityl-imidazol-2-ylidenepalladium(0)-$\eta^2,\eta^2$,-1,1,3,3-tetramethyl-1,3-divinyldisiloxane, $5.5\times10^{-5}$ mol) and 230 mg of 1,3-dimesityl-1H-imidazol-3-ium methanesulfonate ($5.7\times10^{-4}$ mol) in a 1 l Schlenk flask under argon with 140 ml of THF and 120 ml of ethylene glycol (152 g, 2.45 mol). The solution was stirred for half an hour and transferred under argon to a 2 l stainless steel autoclave (Parr Instruments). The autoclave was cooled with dry ice, and 300 g of butadiene (5.5 mol) were condensed in. The autoclave was warmed to room temperature, a pressure of 20 bar being generated with nitrogen. Subsequently it was stirred at 80° C. for 20 hours. After the end of the reaction, the autoclave was cooled, the pressure was let off and the reaction solution was returned to a 1 l Schlenk flask. The product obtained was purified by vacuum distillation, the boiling temperature being approximately 70° C. 248 g (60%) of product were obtained. The product was analysed by means of NMR spectroscopy.

The resulting 2-octa-2,7-dienyloxyethanol was subsequently reacted with methyl methacrylate to give 2-((2-E) octa-2,7-dienyloxy)ethyl 2-methylprop-2-enoate.

For this purpose, 100.0 g (0.59 mol) of 2-octa-2,7-dienyloxyethanol, 590.6 g (5.90 mol) of methyl methacrylate, 0.141 g (1000 ppm) of hydroquinone monomethyl ether (HMQE) and 0.141 g (1000 ppm) of phenothiazine were introduced. The batch was then dewatered azeotropically using methyl methacrylate. Then the catalyst (1.0 g of tetraisopropyl titanate in solution in 1.0 g of methyl methacrylate) was added.

The reaction mixture was heated at boiling. The methyl methacrylate/methanol azeotrope was separated off, the overhead temperature climbing in steps to 100° C. After the end of the reaction the reaction mixture was cooled to about 80° C. After the end of the reaction, the mixture was briefly cooled, the catalyst was precipitated by addition of 20 ml of water, and cooling continued to room temperature with stirring. Following filtration, the excess methyl methacrylate was distilled off on a rotary evaporator.

EXAMPLE 3

Use Example

First of all, in a 1 l PE beaker, 90 g of butyl acrylate (BuA), 78 g of methyl methacrylate (MMA), 30 g of octadienyloxyethyl methacrylate, prepared according to Example 2, 2 g of methacrylic acid (MAA), 1.6 g of ammonium peroxodisulphate (APS), 6.0 g of Disponil FES 32 (30% form), 9.0 g of Triton X305 and 186.3 g of water were emulsified using an Ultra-Turrax at 4000 rpm for 3 minutes.

A 1 l glass reactor which could be maintained at a certain temperature using a water bath and was equipped with a paddle stirrer was charged with 110 g of water and 0.15 g of Disponil FES 32 (30% form) and this initial charge was heated to 80° C. and admixed with 0.15 g of ammonium peroxodisulphate (APS) in solution in 10 g of water. 5 minutes after the addition of the APS, the above-prepared emulsion was metered in over the course of 240 minutes (interval: 3 minutes' feed, 4 minutes' wait, 237 minutes' feed of remainder).

After the end of the feed, stirring was continued at 80° C. for 1 hour. Thereafter the dispersion was cooled to room temperature and filtered off through a VA sieve with a mesh size of 0.09 mm.

The emulsion prepared had a solids content of 40±1%, a pH of 2.3, a viscosity of 12 mPas and a $r_{N5}$ value of 96 nm.

The properties of the resultant coating material were investigated by means of different methods. For this purpose, tests relating to the solvent resistance were determined on dry films, and the residual monomer content was determined on the dispersions.

The solvent resistance was determined using methyl isobutyl ketone (MIBK), a sample being swollen with MIBK for 4 hours at room temperature. The sample was then removed from the solvent, and excess solvent was removed. Subsequently the sample was dried at about 140° C. for 1 hour. The swelling in MIBK was 203%, based on the weight of the sample obtained after the swelling test.

EXAMPLE 4

Use Example

First of all, in a 1 l PE beaker, 95 g of butyl acrylate (BuA), 83.6 g of methyl methacrylate (MMA), 19.4 g of octadienyloxyethyl methacrylate, 2 g of methacrylic acid (MAA), 0.6 g of ammonium peroxodisulphate (APS), 6.0 g of Disponil FES 32 (30% form), 9.0 g of Triton X305 and 186.3 g of water were emulsified using an Ultra-Turrax at 4000 rpm for 3 minutes.

A 1 l glass reactor which could be maintained at a certain temperature using a water bath and was equipped with a paddle stirrer was charged with 110 g of water and 0.15 g of Disponil FES 32 (30% form) and this initial charge was heated to 80° C. and admixed with 0.15 g of ammonium peroxodisulphate (APS) in solution in 10 g of water. 5 minutes after the addition of the APS, the above-prepared emulsion was metered in over the course of 240 minutes (interval: 3 minutes' feed, 4 minutes' wait, 237 minutes' feed of remainder).

After the end of the feed, stirring was continued at 80° C. for 1 hour. Thereafter the dispersion was cooled to room temperature and filtered off through a VA sieve with a mesh size of 0.09 mm.

The emulsion prepared had a solids content of 40±1%, a pH of 2.3, a viscosity of 12 mPas and a $r_{N5}$ value of 93 nm.

The properties of the resultant coating material were investigated by means of different methods. For this purpose, tests relating to the solvent resistance were determined on dry films, and the residual monomer content was determined on the dispersions.

The solvent resistance was determined using methyl isobutyl ketone (MIBK), a sample being swollen with MIBK for 4 hours at room temperature. The sample was then removed from the solvent, and excess solvent was removed. Subsequently the sample was dried at about 140° C. for 1 hour. The swelling in MIBK, taking account of the loss of weight, was 286%.

EXAMPLE 5

Use Example

First of all, in a 1 l PE beaker, 96.6 g of butyl acrylate (BuA), 88.7 g of methyl methacrylate (MMA), 12.7 g of octadienyloxyethyl methacrylate, 2 g of methacrylic acid (MAA), 0.6 g of ammonium peroxodisulphate (APS), 6.0 g of Disponil FES 32 (30% form), 9.0 g of Triton X305 and 186.3 g of water were emulsified using an Ultra-Turrax at 4000 rpm for 3 minutes.

A 1 l glass reactor which could be maintained at a certain temperature using a water bath and was equipped with a paddle stirrer was charged with 110 g of water and 0.15 g of Disponil FES 32 (30% form) and this initial charge was heated to 80° C. and admixed with 0.15 g of ammonium peroxodisulphate (APS) in solution in 10 g of water. 5 minutes after the addition of the APS, the above-prepared emulsion was metered in over the course of 240 minutes (interval: 3 minutes' feed, 4 minutes' wait, 237 minutes' feed of remainder).

After the end of the feed, stirring was continued at 80° C. for 1 hour. Thereafter the dispersion was cooled to room temperature and filtered off through a VA sieve with a mesh size of 0.09 mm.

The emulsion prepared had a solids content of 40±1%, a pH of 2.3, a viscosity of 13 mPas and a $r_{N5}$ value of 92 nm.

The properties of the resultant coating material were investigated by means of different methods. For this purpose, tests relating to the solvent resistance were determined on dry films, and the residual monomer content was determined on the dispersions.

The solvent resistance was determined using methyl isobutyl ketone (MIBK), a sample being swollen with MIBK for 4 h at room temperature. The sample was then removed from the solvent and excess solvent was removed. Subsequently the sample was dried at about 140° C. for 1 h. The swelling in MIBK on the basis of the weight loss amounted to 304%.

COMPARATIVE EXAMPLE 1

First of all, in a 2 l PE beaker, 216 g of butyl acrylate (BuA), 180 g of methyl methacrylate (MMA), 4 g of methacrylic acid (MAA), 1.2 g of ammonium peroxodisulphate (APS), 12.0 g of Disponil FES 32 (30% form) and 359.18 g of water were emulsified using an Ultra-Turrax at 4000 rpm for 3 minutes.

A 2 l glass reactor which could be maintained at a certain temperature using a water bath and was equipped with a paddle stirrer was charged with 230 g of water and 0.3 g of Disponil FES 32 (30% form) and this initial charge was heated to 80° C. and admixed with 0.3 g of ammonium peroxodisulphate (APS) in solution in 10 g of water. 5 minutes after the addition of the APS, the above-prepared emulsion was metered in over the course of 240 minutes (interval: 3 minutes' feed, 4 minutes' wait, 237 minutes' feed of remainder).

After the end of the feed, stirring was continued at 80° C. for 1 hour. Thereafter the dispersion was cooled to room temperature and filtered off through a VA sieve with a mesh size of 0.09 mm.

The properties of the resultant coating material were investigated by means of different methods. For this purpose, tests relating to the solvent resistance were determined on dry films, and the residual monomer content was determined on the dispersions.

The dried film was completely soluble in MIBK. Consequently, no solvent uptake could be determined.

The invention claimed is:

1. A (meth)acrylate monomer of formula (I)

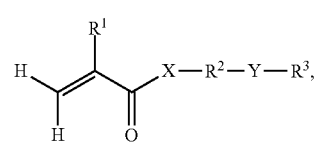

wherein
R¹ is hydrogen or a methyl group,
X is oxygen or a group of NR' wherein R' is hydrogen or a radical having 1 to 6 carbon atoms,
R² is an alkylene group having 1 to 22 carbon atoms,
Y is oxygen, sulphur, or a group of NR", wherein R" represents hydrogen or a radical having 1 to 6 carbon atoms, and
R³ is an unsaturated radical having 8 carbon atoms and at least two C—C double bonds which are not part of an aromatic system.

2. The (meth)acrylate monomer according to claim 1, wherein R² is an ethylene group.

3. The (meth)acrylate monomer according to claim 1, wherein R³ comprises a terminal double bond.

4. The (meth)acrylate monomer according to claim 1, wherein R³ does not comprise any terminal double bonds.

5. The (meth)acrylate monomer according to claim 1, wherein R³ comprises precisely two double bonds.

6. The (meth)acrylate monomer according to claim 1, wherein the double bonds present in R³ are conjugated.

7. The (meth)acrylate monomer according to claim 1, wherein the double bonds present in R³ are not conjugated.

8. The (meth)acrylate monomer according to claim 1, having an iodine number in a range from 100 to 400 g iodine/100 g.

9. A monomer mixture, comprising at least one (meth) acrylate monomer according to claim 1.

10. The monomer mixture according to claim 9, further comprising at least one monomer A which comprises at least one ester group and is different from the at least one (meth) acrylate monomer of formula (I).

11. The monomer mixture according to claim 10, comprising at least one selected from the group consisting of a (meth) acrylate, a fumarate, a maleate, and a vinyl acetate.

12. The monomer mixture according to claim 9, wherein the monomer mixture comprises at least one monomer having an acid group.

13. The monomer mixture according to claim 9, comprising:
   0.1% to 90% by weight of the at least one (meth)acrylate monomer of formula (I);
   10% to 95% by weight of at least one monomer A comprising ester group;
   0% to 10% by weight of at least one monomer having an acid group;
   0% to 50% by weight of at least one styrene monomer; and
   0% to 50% by weight of at least one further comonomer.

14. A polymer, comprising at least one unit comprising the monomer according to claim 1 in reacted form.

15. The polymer obtained by polymerizing the monomer mixture according to claim 9.

16. The polymer according to claim 14, having a glass transition temperature in a range from −20 to 40° C.

17. The polymer according to claim 14, in the form of an emulsion polymer.

18. A coating material, comprising the polymer according to claim 14.

19. A coating material comprising an alkyd resin which has been modified with the monomer according to claim 1.

20. The coating material according to claim 18, further comprising an alkyd resin.

21. The coating material according to claim 18, in the form of an aqueous dispersion.

22. A process for preparing the monomer according to claim 1, the process comprising:
    reacting
    a reactant of formula (II)

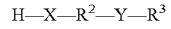   (II), wherein
    X is oxygen or a group of formula NR' wherein R' is hydrogen or a radical having 1 to 6 carbon atoms,
    $R^2$ is an alkylene group having 1 to 22 carbon atoms,
    Y is oxygen, sulphur, or a group of formula NR", in which wherein R" represents hydrogen or a radical having 1 to 6 carbon atoms, and
    $R^3$ is an at least doubly unsaturated radical having 8 carbon atoms,
    with at least one selected from the group consisting of a (meth)acrylate and (meth)acrylic acid.

* * * * *